United States Patent
Naito et al.

(10) Patent No.: US 9,632,014 B2
(45) Date of Patent: Apr. 25, 2017

(54) METHOD AND APPARATUS FOR DETECTING DEGRADATION OF RESIN FILM

(71) Applicants: Shinya Naito, Chiyoda-ku (JP);
Chinatsu Sanda, Chiyoda-ku (JP);
Masahiko Hida, Chiyoda-ku (JP);
Michio Murai, Chiyoda-ku (JP)

(72) Inventors: Shinya Naito, Chiyoda-ku (JP);
Chinatsu Sanda, Chiyoda-ku (JP);
Masahiko Hida, Chiyoda-ku (JP);
Michio Murai, Chiyoda-ku (JP)

(73) Assignee: Mitsubushi Electric Corporation, Tokyo (JP)

(*) Notice: Subject to any disclaimer, the term of this patent is extended or adjusted under 35 U.S.C. 154(b) by 173 days.

(21) Appl. No.: 14/368,078

(22) PCT Filed: Jan. 11, 2013

(86) PCT No.: PCT/JP2013/050401
§ 371 (c)(1),
(2) Date: Jun. 23, 2014

(87) PCT Pub. No.: WO2013/128956
PCT Pub. Date: Sep. 6, 2013

(65) Prior Publication Data
US 2014/0366639 A1 Dec. 18, 2014

(30) Foreign Application Priority Data
Feb. 27, 2012 (JP) ................. 2012-039696

(51) Int. Cl.
*G01N 3/08* (2006.01)
*B66B 7/12* (2006.01)
(Continued)

(52) U.S. Cl.
CPC .............. *G01N 3/08* (2013.01); *B66B 7/1215* (2013.01); *G01N 19/04* (2013.01);
(Continued)

(58) Field of Classification Search
CPC ........................................................ G01N 3/08
(Continued)

(56) References Cited

U.S. PATENT DOCUMENTS 5,174,160 A 12/1992 Morita et al.
7,036,298 B2 * 5/2006 Honda ................ B66B 7/06
57/214

(Continued)

FOREIGN PATENT DOCUMENTS

CN 103698199 A 4/2014
DE 122 722 10/1976
(Continued)

OTHER PUBLICATIONS

International Search Report Issued Mar. 19, 2013 in PCT/JP13/050401 Filed Jan. 11, 2013.
(Continued)

*Primary Examiner* — Lisa Caputo
*Assistant Examiner* — Octavia Hollington
(74) *Attorney, Agent, or Firm* — Oblon, McClelland, Maier & Neustadt, L.L.P.

(57) ABSTRACT

A method for detecting degradation of resin film detects whether a resin coated rope having a circumferential portion coated with resin film has the resin film degraded. The method for detecting degradation of resin film includes: winding a wire on a circumferential portion of the resin coated rope; applying tension to the wire to compress the resin film in a radial direction of the resin coated rope; and comparing a first relationship with a second relationship to determine how the resin film is degraded, the first relation-
(Continued)

ship indicating a relationship between the tension of the wire and how much amount the resin film has compressed, as obtained in the applying, the second relationship indicating a relationship between the tension of the wire and how much amount the resin film has compressed, as predetermined as a reference.

8 Claims, 5 Drawing Sheets

(51) Int. Cl.
    *G01N 19/04*     (2006.01)
    *G01N 33/00*     (2006.01)
(52) U.S. Cl.
    CPC ........... *G01N 2033/0096* (2013.01); *G01N 2203/0266* (2013.01); *G01N 2203/0282* (2013.01)
(58) Field of Classification Search
    USPC ............................................. 73/818
    See application file for complete search history.

(56) References Cited

U.S. PATENT DOCUMENTS

| | | | | |
|---|---|---|---|---|
| 7,137,483 B2* | 11/2006 | Kato | ............ | B66B 7/06 187/251 |
| 7,565,791 B2* | 7/2009 | Itaya | ............ | D07B 1/0673 57/237 |
| 8,023,789 B2* | 9/2011 | Aoyagi | ............ | G02B 1/045 385/100 |
| 8,402,731 B2* | 3/2013 | Naito | ............ | B66B 7/06 57/210 |
| 9,162,849 B2* | 10/2015 | Mitsui | ............ | B66B 7/06 |
| 2001/0025743 A1 | 10/2001 | Ach | | |
| 2010/0009184 A1 | 1/2010 | Bruyneel et al. | | |

FOREIGN PATENT DOCUMENTS

| | | |
|---|---|---|
| EP | 2 578 527 A1 | 4/2013 |
| JP | 62 132145 | 6/1987 |
| JP | 7 134095 | 5/1995 |
| JP | 2001 99776 | 4/2001 |
| JP | 2002 62232 | 2/2002 |
| JP | 2007-111589 | 5/2007 |
| JP | 2008 96315 | 4/2008 |
| JP | 2009 143678 | 7/2009 |
| JP | 2010-515833 A | 5/2010 |
| JP | 2011 220886 | 11/2011 |
| WO | WO 2011/148469 A1 | 12/2011 |

OTHER PUBLICATIONS

Office Action issued Sep. 24, 2015 in Korean Patent Application No. 10-2014-7023662 (with English language translation).
Office Action issued Oct. 13, 2015 in Japanese Patent Application No. 2014-502057 (with English translation).
Korean Office Action issued in Patent Application No. 10-2016-7016969 on Aug. 19, 2016 (w/English translation).
Office Action issued Dec. 11, 2015 in Chinese patent Application No. 201380011063.0 (with English translation and English translation of category of cited documents).
German Office Action issued in Application No. 11 2013 001 170.0 on Dec. 5, 2016 (w/ English translation).

* cited by examiner

METHOD AND APPARATUS FOR DETECTING DEGRADATION OF RESIN FILM

TECHNICAL FIELD

The present invention relates to a method and apparatus for detecting degradation of resin film, and more specifically to a method and apparatus for detecting whether a resin coated rope circumferentially coated with resin film has the resin film degraded.

BACKGROUND ART

A rope used to move a cage of an elevator up and down is fatigued and/or worn and as a result has its constituent steel wires broken one after another. Accordingly, after the elevator has been installed, the elevator undergoes a periodical inspection to confirm which portion the steel wires have broken or how many of the steel wires are broken visually or with a measuring instrument to evaluate the rope for safety.

In recent years, as hoists are reduced in size and sheaves are reduced in diameter, a resin coated rope for example having a circumference coated with thermoplastic polyurethane elastomer or a similar excellently elastic resin is increasingly used. An elevator with a resin coated rope receives power from a hoist and transmits it to a cage through the rope via the coating of resin, and accordingly, the coating of resin is required to have a large mechanical strength, and a satisfactory friction characteristic for the hoist's sheave. Accordingly, the elevator with the resin coated rope entails a periodical inspection conducted not only to confirm whether the rope has its steel wires broken but also to confirm whether the rope has its coating of resin degraded.

Whether a resin coated rope has its coating of resin degraded is detected in a method proposed for example as follows: whether a steel wire that configures the rope and a sheave have established electrical conduction therebetween is detected to detect whether the coating of resin is damaged (see Japanese Patent Laying-Open No. 2009-143678 (PTD 1) for example). Furthermore, whether a urethane roll circumferentially coated with polyurethane resin is degraded is non-destructively detected in a method proposed as follows: the urethane roll's indentation hardness is measured to obtain how much in degree the indentation hardness as measured is different from that of the urethane roll as measured when it was an unused product, and therefrom whether the urethane roll is degraded is detected (see Japanese Patent Laying-Open No. 2002-062232 (PTD 2) for example).

CITATION LIST

Patent Documents

PTD 1: Japanese Patent Laying-Open No. 2009-143678
PTD 2: Japanese Patent Laying-Open No. 2002-062232

SUMMARY OF INVENTION

Technical Problem

The degradation detection method proposed in PTD 1 is effective as a method for detecting whether a resin coated rope has its coating of resin damaged. This method, however, is a method that can detect whether a coating of resin that is for example abraded and accordingly significantly worn or torn is damaged. As has been described above, an elevator that employs a resin coated rope drives its cage via a coefficient of friction between the coating of resin and the hoist's sheave. Accordingly, when the coating of resin is damaged to such an extent that the steel wire and the sheave establish electrical conduction, it does not ensure sufficient frictional force with the sheave, resulting in an increased possibility of the elevator having a defect, causing an accident, or the like. Accordingly, in view of ensuring the elevator's safety, there is a demand for a method for detecting with higher precision how a coating of resin is degraded.

While the degradation detection method proposed in PTD 2 is not a method for detecting whether a resin coated rope is degraded, the method is effective as a method for non-destructively detecting whether a coating of resin is degraded. This method, however, requires that a coating of resin to be inspected should have a sufficient thickness and a uniform thickness distribution. A resin coated rope, however, has a coating of resin small in thickness and also having a varying thickness distribution attributed to its internal, twisted steel wire bundle, and it is thus difficult to employ the method to detect with high precision whether the coating of resin is degraded.

The present invention has been made in view of the above issue, and contemplates a method and apparatus for detecting with high precision and non-destructively whether a resin coated rope has a resin film degraded.

Solution to Problem

The present invention provides a method for detecting degradation of resin film to detect whether a resin coated rope having a circumferential portion coated with resin film has the resin film degraded. The method includes the steps of: winding a linear object on the circumferential portion of the resin coated rope; applying tension to the linear object to compress the resin film in a radial direction of the resin coated rope; and comparing a first relationship with a second relationship to determine how the resin film is degraded, the first relationship indicating a relationship between the tension of the linear object and how much amount the resin film has compressed, as obtained in the step of applying, the second relationship indicating a relationship between the tension of the linear object and how much amount the resin film has compressed, as predetermined as a reference.

The present invention thus provides a method for detecting how the resin film is degraded from a relationship between the tension applied to the linear object wound on the circumferential portion of the resin coated rope and how much amount the resin film has compressed. The present invention can thus provide a method for detecting degradation of resin film, that can detect with high precision and non-destructively whether a resin coated rope has a resin film degraded that is small in thickness and has a varying distribution in thickness.

The present invention provides an apparatus for detecting degradation of resin film to detect whether a resin coated rope having a circumferential portion coated with resin film has the resin film degraded. The apparatus includes: a securing unit that fixes a relative positional relationship between the resin coated rope and the apparatus; a holding unit capable of holding a linear object wound on the circumferential portion of the resin coated rope; a tensioning unit applying tension to the linear object; a tension detection unit that detects the tension applied to the linear object; and a displacement detection unit that detects how much amount the linear object has displaced.

The present apparatus that detects degradation of resin film, that is configured as described above, can be used in the present method for detecting degradation of resin film. The present invention can thus provide an apparatus to detect degradation of resin film, that can detect with high precision and non-destructively whether a resin coated rope has a resin film degraded that is small in thickness and has a varying distribution in thickness.

Advantageous Effect of Invention

As is apparent from the above, the present method and apparatus can thus provide a method and apparatus capable of detecting with high precision and non-destructively whether a resin coated rope has a resin film degraded.

DESCRIPTION OF EMBODIMENTS

Hereinafter reference will be made to the drawings to describe the present invention in embodiments. In the figures, identical or corresponding components are identically denoted and will not be described repeatedly.

First Embodiment

Figure 1:
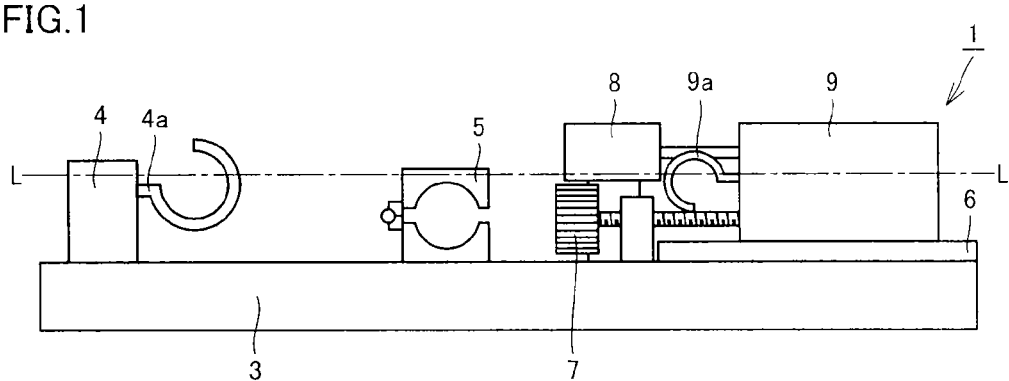
FIG. 1 is a schematic side view in configuration of a degradation detection apparatus of first, second and third embodiments.
Figure 2:
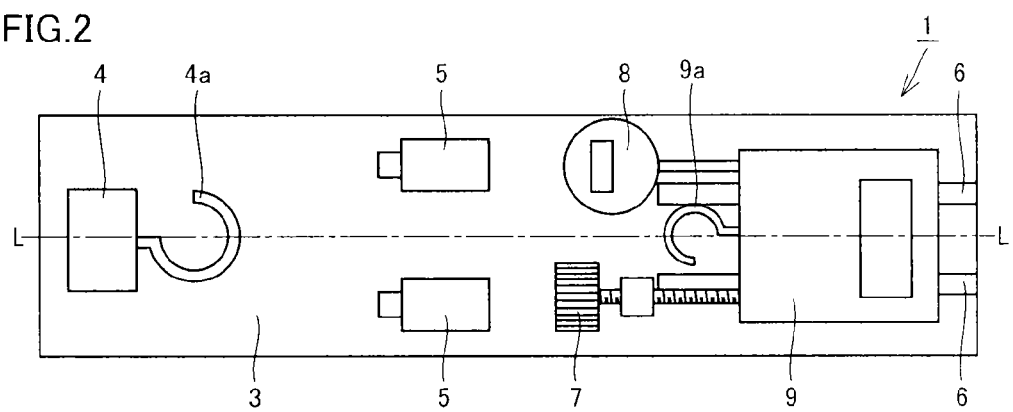
FIG. 2 is a schematic top view in configuration of the degradation detection apparatus of the first, second and third embodiments.

Initially, the present invention in one, first embodiment will be described. Initially will be described a degradation detection apparatus of the present embodiment to detect degradation of resin film. The present embodiment provides a degradation detection apparatus 1 to detect degradation of resin film to detect whether a resin coated rope having a circumferential portion coated with resin film has the resin film degraded. With reference to FIG. 1 and FIG. 2, degradation detection apparatus 1 mainly includes a mount 3, a hook support 4, hooks 4a and 9a serving as a holding unit, a rope securing unit 5, a linear guide 6, a feed screw 7 serving as a tensioning unit, a displacement gauge 8 serving as a displacement detection unit, and a tension gauge 9 serving as a tension detection unit.

On mount 3 are disposed hook support 4 to support hook 4a, a plurality of rope securing units 5, and linear guide 6. On linear guide 6 is disposed tension gauge 9. Tension gauge 9 has hook 9a attached thereto. Furthermore, tension gauge 9 is provided with displacement gauge 8 to thereby allow how much amount tension gauge 9 has displaced to be measurable. Furthermore, tension gauge 9 also has feed screw 7 attached thereto, and feed screw 7 can be turned to move tension gauge 9 on linear guide 6 axially. Furthermore, as shown in FIG. 2, rope securing unit 5 is located between hook support 4 and linear guide 6. Furthermore, linear guide 6 is disposed on mount 3 such that linear guide 6 has an axis in a direction parallel to a virtual straight line L-L connecting hook 4a and hook 9a. Furthermore, a plurality of (or two) rope securing units 5 are aligned on mount 3 in a direction transverse to virtual straight line L-L, more specifically perpendicular thereto.

Rope securing unit 5 fixes a relative positional relationship between a resin coated rope to be inspected and degradation detection apparatus 1. For example an installed elevator (not shown) does not have its resin coated rope removed and degradation detection apparatus 1 is instead moved and the resin coated rope is held by rope securing unit 5 to fix degradation detection apparatus 1 relative to the resin coated rope.

Hooks 4a and 9a hold a wire or the like that is a linear object wound on a circumferential portion of the resin coated rope to be secured to rope securing unit 5. Specifically, hooks 4a and 9a each hold an opposite end of the wire wound on the circumferential portion of the resin coated rope. Furthermore, as shown in FIG. 1, hook 4a and hook 9a are disposed at such a level that allows virtual straight line L-L to be a tangent to a circular cross section of the resin coated rope to be secured to rope securing unit 5 and is adjustable as appropriate by varying the resin coated rope's outer diameter.

Tension gauge 9 can be displaced on linear guide 6 axially by turning feed screw 7. In other words, feed screw 7 can be operated to allow the wire wound on the circumferential portion of the resin coated rope to have one end thereof that is held by hook 9a displaced to tension the wire. This allows the resin coated rope to have the circumferential coating of resin film compressed. Note that degradation detection apparatus 1 may have feed screw 7 replaced with a small servo-motor or a similar electrical mechanism allowing tension gauge 9 to be displaceable.

Tension gauge 9 detects how much tension is applied to the wire held by hooks 4a and 9a. Displacement gauge 8 detects how much amount the wire held by hooks 4a and 9a has displaced.

Hereinafter will be described a method according to the present embodiment for detecting degradation of resin film. The present embodiment provides a degradation detection method that is a method for detecting degradation of resin film, that is a method for detecting whether a resin coated rope having a circumferential portion coated with resin film has the resin film degraded, and the method is performed for example by employing degradation detection apparatus 1 of the present embodiment as described above.

Figure 3:
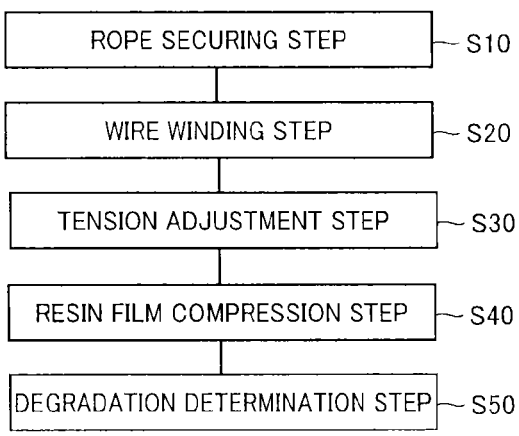
FIG. 3 is a flowchart outlining a degradation detection method.
Figure 4:
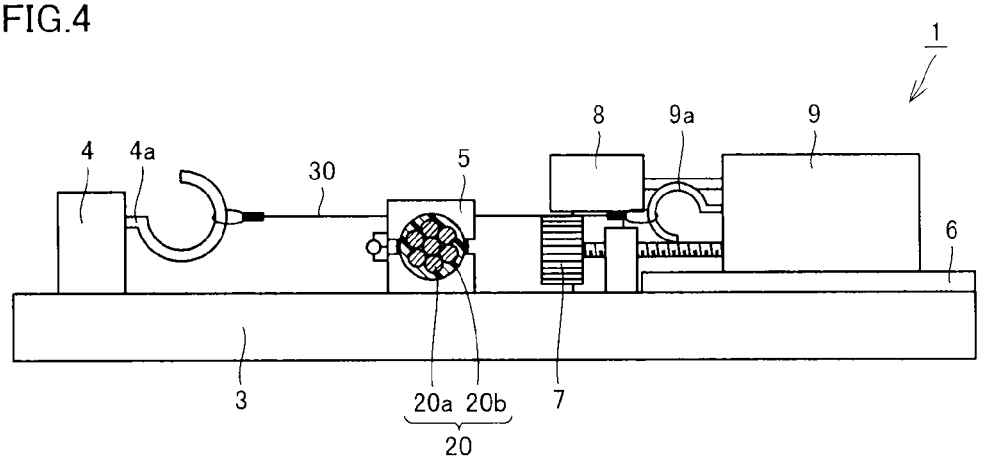
FIG. 4 is a schematic side view for illustrating a degradation detection method of the first, second and third embodiments.
Figure 5:
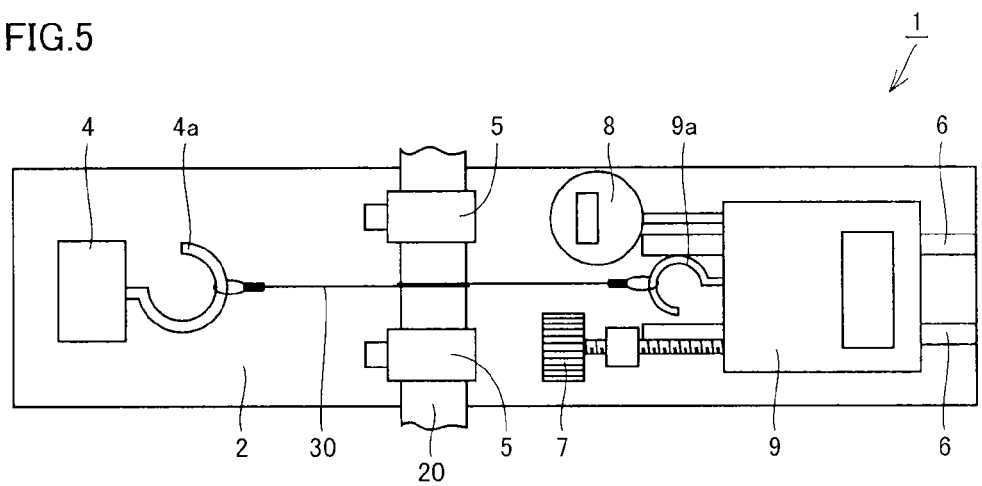
FIG. 5 is a schematic top view for illustrating the degradation detection method of the first, second and third embodiments.

With reference to FIG. 3, initially, as a step (S10), a rope securing step is performed. In this step (S10), with reference to FIG. 4 and FIG. 5, an elevator (not shown) installed in a building or the like has a resin coated rope 20 secured to degradation detection apparatus 1 at rope securing unit 5. After resin coated rope 20 is completely secured, tension gauge 9 has its tension value corrected to zero.

In this step (S10), resin coated rope 20 for example having an outer diameter of 12.5 mm and formed of a plurality of steel wires 20a and a resin film 20b coating a circumferential portion thereof is secured to rope securing unit 5 as an object to be inspected. Resin film 20b may be formed for example of thermoplastic polyurethane elastomer or the like. Furthermore, resin coated rope 20 can be secured without the necessity of removing the rope from the sheave of the elevator or cutting the rope to have a predetermined length. In other words, degradation detection apparatus 1 is moved to secure resin coated rope 20 to rope securing unit 5.

Then as a step (S20) a wire winding step is performed. In this step (S20), with reference to FIG. 4 and FIG. 5, a linear object implemented as a wire 30 as is wound on a circumferential portion of resin coated rope 20. Furthermore, wire 30 thus wound has opposite ends engaged with and thus held by hooks 4a and 9a, respectively. Furthermore, the linear object may be any object that has a prescribed strength and can be wound on the circumferential portion of resin coated rope 20, as wire 30 does and can, and it may not be wire and may instead be in the form for example of a tape, a ribbon or the like.

In this step (S20), wire 30 has an outer diameter preferably of 0.1 mm to 1.0 mm, more preferably 0.25 mm to 0.5 mm. Furthermore, wire 30 may have any length that allows the wire to be wound on the circumferential portion of resin coated rope 20 and also have its opposite ends engaged with and thus held by hooks 4a and 9a. While wire 30 excessively large in length does not negatively affect detecting whether resin film 20b is degraded, such wire 30 would require that degradation detection apparatus 1 be increased in size. For this ground, wire 30 has a length preferably of 100 mm to 500 mm, more preferably 200 mm to 300 mm.

Figure 6:
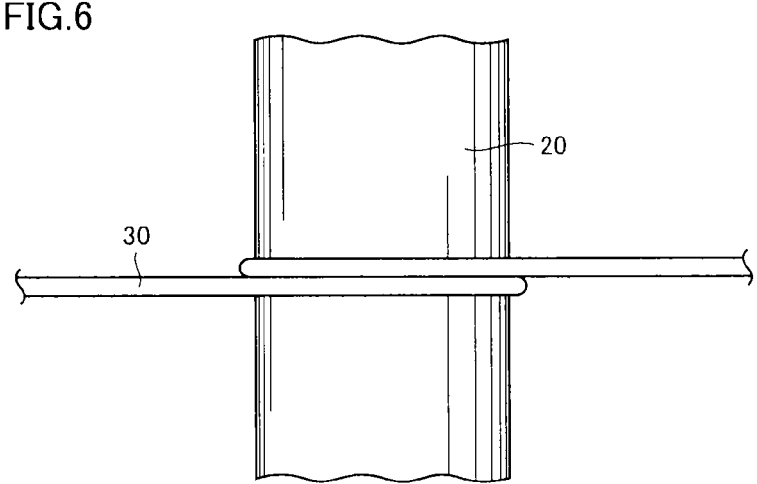
FIG. 6 is a schematic diagram for illustrating the degradation detection method of the first, second and third embodiments.
Figure 7:
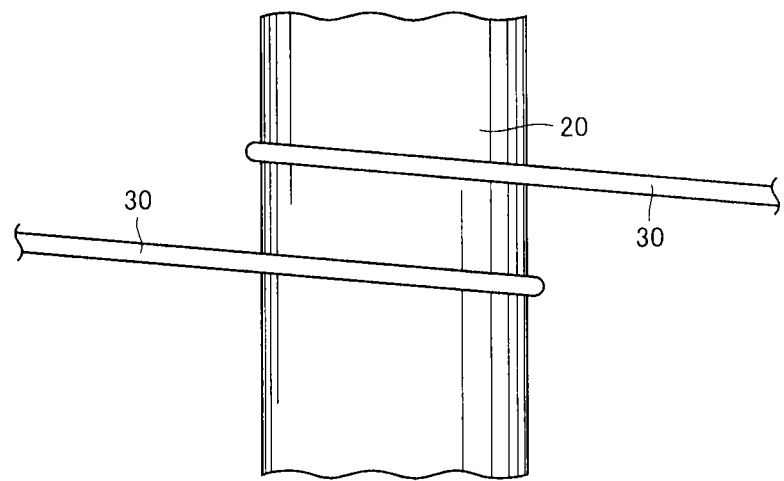
FIG. 7 is a schematic diagram for illustrating the degradation detection method of the first, second and third embodiments.

With reference to FIG. 6, preferably, wire 30 is brought into contact with resin film 20b parallel to a direction in which wire 30 is pulled, and wire 30 is thus wound on the circumferential portion of resin coated rope 20 Furthermore, more preferably, wire 30 is wound on the circumferential portion of resin coated rope 20 in contact with resin film 20b along a length that approximates to a circumferential length of resin coated rope 20. This facilitates bringing wire 30 into contact with resin film 20b along a fixed length in detecting more than once whether resin film 20b is degraded. This can limit an effect of a noise resulting from a frictional force generated at those portions of wire 30 and resin film 20b, respectively, in contact with each other, and thus allows more sensitive degradation detection. For this ground, winding wire 30 obliquely relative to the direction in which wire 30 is pulled, as shown in FIG. 7, is unpreferable in view of bringing wire 30 into contact with resin film 20b along a fixed length.

Figure 8:
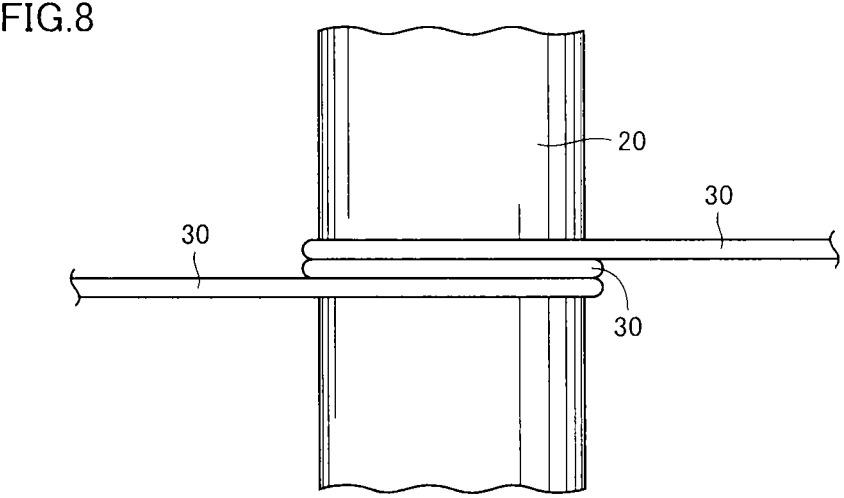
FIG. 8 is a schematic diagram for illustrating the degradation detection method of the first, second and third embodiments.

Furthermore, as the frictional force generated at those portions of wire 30 and resin film 20b, respectively, in contact with each other, serves as a cause of a noise, preferably, wire 30 is wound on the circumferential portion of resin coated rope 20 only by a single turn. This allows degradation to be detected while limiting the noise. Accordingly, providing a plurality of turns of wire 30 wound on the circumferential portion of resin coated rope 20, as shown in FIG. 8, is unpreferable in view of limiting the noise.

Then, as a step (S30), a tension adjustment step is performed. In this step (S30), feed screw 7 is adjusted to displace wire 30 to slightly tension wire 30. Then, after the tension adjustment is completed, tension gauge 9 and displacement gauge 8 have a tension value and a displacement value, respectively, corrected to zero. In doing so, wire 30 experiences a tension preferably of 0.1 N to 1 N, more preferably 0.4 N to 0.6 N. This facilitates winding wire 30 on the circumferential portion of resin coated rope 20 in a preferable condition, as has been described with reference to FIG. 6.

Then as a step (S40) a resin film compression step is performed. In this step (S40), feed screw 7 is turned to displace hooks 4a and 9a along the axis of linear guide 6 to displace wire 30, as prescribed. More specifically, feed screw 7 is turned to allow wire 30 to have displaced, as prescribed, an end that is held by hook 9a. This tensions wire 30, which in turn compresses resin film 20b in a radial direction of resin coated rope 20. How much amount wire 30 has displaced, i.e., how much amount resin film 20b has compressed, is detected by displacement gauge 8, and how much tension is applied to wire 30 is detected by tension gauge 9.

Furthermore, in this step (S40), wire 30 is displaced as prescribed, i.e., resin film 20b is compressed by an amount preferably of 0.2 mm to 2 mm, more preferably 0.5 mm to 1 mm. If wire 30 has a displacement smaller than the above range, wire 30 does not bite into resin film 20b and may insufficiently be tensioned. In contrast, if wire 30 has a displacement larger than the above range, wire 30 is tensioned beyond a load that breaks wire 30, and wire 30 may be broken or leave its bite mark on resin film 20b.

Then as a step (S50) a degradation determination step is performed. In this step (S50), a first relationship indicating a relationship between the tension of wire 30 and how much amount resin film 20b has compressed, as obtained in step (S40), is compared with a second relationship indicating a relationship between the tension of wire 30 and how much amount resin film 20b has compressed, as predetermined as a reference, to determine how resin film 20b is degraded. More specifically, a tension value (F) of wire 30 required, as detected in step (S40), to compress resin film 20b by a prescribed amount is compared with a tension value ($F_0$) of wire 30 required, as previously determined as a reference, to compress resin film 20b by the prescribed amount to determine how resin film 20b is degraded. In the present embodiment the method for detecting degradation of resin film for example uses values F and $F_0$ to calculate a rate of change in tension (in %)=$|F_0-F|/F_0 \times 100$ to determine how resin film 20b is degraded. Specifically, when a rate of change in tension calculated exceeds a prescribed value, it is determined that the rope should be repaired, replaced or similarly handled.

Furthermore, the reference value, or tension value ($F_0$), may be a tension value of wire 30 required to compress resin film 20b of resin coated rope 20 that is unused by the prescribed amount. This facilitates setting the reference value.

Thus the present embodiment provides a method for detecting degradation of resin film to detect whether resin coated rope 20 has resin film 20b degraded, as follows: Initially, wire 30 is wound on the circumferential portion of resin coated rope 20 and tensioned to compress resin film 20b. The tension of wire 30 in compressing resin film 20b has a relationship with how much amount resin film 20b has compressed, and this relationship is compared with a relationship between the tension of wire 30 and how much amount resin film 20b has compressed, that is predetermined as a reference, to determine how resin film 20b is degraded. Thus the present embodiment provides a method for detecting degradation of resin film, that allows how resin film 20b is degraded to be determined from a relationship between how much tension is applied to wire 30 wound on the circumferential portion of resin coated rope 20 and how much amount wire 30 has displaced as it is tensioned, i.e., how much amount resin film 20b has compressed. Thus the present embodiment provides a method for detecting degradation of resin film, that can detect with high precision and non-destructively whether resin coated rope 20 has resin film 20b degraded that is small in thickness and has a varying distribution in thickness.

Furthermore, the present method according to the present embodiment for detecting degradation of resin film can be employed to periodically inspect an elevator so that a value of a rate of change in tension calculated in step (S50) can be used to provide inspection and maintenance such as determining when resin coated rope 20 should be replaced with another such rope. Note that when resin coated rope 20 should be replaced with another such rope is determined preferably with reference to a value of a rate of change in tension determined through a separate, detailed evaluation as the value varies with the specifications of resin coated rope 20, the material(s) of resin film 20b, and the like. Furthermore, the present method according to the present embodiment for detecting degradation of resin film may not only be employed to periodically inspect an elevator but also to inspect resin coated rope 20 in quality when it is shipped as a product, and the method can thus facilitate screening an initial defective product before it is shipped.

Furthermore, the degradation detection method of the present embodiment can be performed by employing degradation detection apparatus 1 of the present embodiment described above. Thus the present embodiment provides degradation detection apparatus 1 that can detect degradation of resin film to detect with high precision and non-destructively whether resin coated rope 20 has resin film 20b degraded that is small in thickness and has a varying distribution in thickness.

Second Embodiment

Hereinafter, the present invention in another, second embodiment will be described. The present embodiment provides a degradation detection apparatus to detect degradation of resin film, that is similar in configuration to the first embodiment's degradation detection apparatus 1 detecting degradation of resin film, and that is as effective as degradation detection apparatus 1 of the first embodiment. Furthermore, the present embodiment provides a method for detecting degradation of resin film, that basically includes steps similar to those of that according to the first embodiment for detecting degradation of resin film and that is as effective as the method according to the first embodiment. The method according to the present embodiment, however, is different from that of the first embodiment in how it determines how resin film is degraded.

Hereinafter will be described a method according to the present embodiment for detecting degradation of resin film. The degradation detection method of the present embodiment is performed for example by employing degradation detection apparatus 1, similarly as has been described in the first embodiment. With reference to FIG. 3 to FIG. 8, steps (S10) to (S30) are initially performed, similarly as has been described in the first embodiment.

Then as step (S40) a resin film compression step is performed In this step (S40), feed screw 7 is turned to displace hooks 4a and 9a along the axis of linear guide 6. Wire 30 thus has one end thereof that is held by hook 9a displaced until wire 30 is tensioned as prescribed. This compresses resin film 20b in the radial direction of resin coated rope 20. How much amount wire 30 has displaced, i.e., how much amount resin film 20b has compressed, is detected by displacement gauge 8, and how much tension is applied to wire 30 is detected by tension gauge 9.

In this step (S40), wire 30 must be tensioned, as prescribed, in a range set to avoid breaking wire 30, and for example when wire 30 has an outer diameter of 0.25 mm, wire 30 is pulled by a tension preferably of 3 N to 15 N, and more preferably 5 N to 10 N. If the tension is smaller than the above range, wire 30 may insufficiently bite into resin film 20b, resulting in reduced precision in detecting degradation. If the tension is larger than the above range, wire 30 may leave its bite mark on resin film 20b.

Then as step (S50) a degradation determination step is performed. In this step (S50), how much amount resin film 20b is required to have compressed to tension wire 30, as prescribed (hereinafter also referred to as a displacement required L), is compared with how much amount resin film 20b is required to have compressed, as previously determined as a reference, to tension wire 30, as prescribed (hereinafter also referred to as a displacement required $L_0$), to determine how resin film 20b is degraded. In the present embodiment the method for detecting degradation of resin film for example uses values L and $L_0$ to calculate a rate of change in displacement required (in %)=$|L_0-L|/L_0 \times 100$ to determine how resin film 20b is degraded. Specifically, when a rate of change in displacement required exceeds a prescribed value, it is determined that the rope should be repaired, replaced or similarly handled. Note that how much amount resin film 20b is required to have compressed that serves as the reference value (i.e., displacement required $L_0$) may be adopted similarly as has been described in the first embodiment, i.e., it may be how much amount resin film 20b of resin coated rope 20 that is unused is required to have compressed to tension wire 30, as prescribed The present embodiment provides a method for detecting degradation of resin film, that compares how much amount resin film 20b is required to have compressed to tension wire 30, as prescribed (i.e., displacement required L), with how much amount resin film 20b is required to have compressed, as previously determined as a reference, to tension wire 30, as prescribed (i.e., displacement required $L_0$), to determine how resin film 20b is degraded. Thus the present embodiment provides a method for detecting degradation of resin film, that can detect with high precision and non-destructively whether resin coated rope 20 has resin film 20b degraded, while allowing wire 30 to be tensioned, as prescribed, by a load set below that which breaks wire 30 to ensure avoiding breaking wire 30.

Third Embodiment

Hereinafter, the present invention in another, third embodiment will be described. The present embodiment provides a degradation detection apparatus to detect degradation of resin film, that is similar in configuration to the first embodiment's degradation detection apparatus 1 detecting degradation of resin film, and that is as effective as degradation detection apparatus 1 of the first embodiment. Furthermore, the present embodiment provides a method for detecting degradation of resin film, that basically includes steps similar to those of that according to the first embodiment for detecting degradation of resin film and that is as effective as the method according to the first embodiment. The method according to the present embodiment, however, is different from that of the first embodiment in how it determines how resin film is degraded.

Hereinafter will be described a method according to the present embodiment for detecting degradation of resin film. The degradation detection method of the present embodiment is performed for example by employing degradation detection apparatus 1, similarly as has been described in the first embodiment. With reference to FIG. 3 to FIG. 8, steps (S10) to (S30) are initially performed, similarly as has been described in the first embodiment.

Then as step (S40) a resin film compression step is performed. In this step (S40), feed screw 7 is turned to displace hooks 4a and 9a along the axis of linear guide 6. Wire 30 thus has one end thereof that is held by hook 9a displaced until wire 30 is tensioned as prescribed. This compresses resin film 20b in the radial direction of resin coated rope 20. How much amount wire 30 has displaced, i.e., how much amount resin film 20b has compressed, is detected by displacement gauge 8, and how much tension is applied to wire 30 is detected by tension gauge 9 Furthermore, thereafter, how much amount wire 30 has displaced as it is tensioned as prescribed is held for a predetermined period of time, and thereafter, how much tension is at that time applied to wire 30 is read by tension gauge 9 and recorded.

In this step (S40), wire 30 must be tensioned, as prescribed, in a range set to avoid breaking wire 30, and for example when wire 30 has an outer diameter of 0.25 mm, wire 30 is pulled by a tension preferably of 3 N to 15 N, and more preferably 5 N to 10 N. If the tension is smaller than the above range, wire 30 may insufficiently bite into resin film 20b, resulting in reduced precision in detecting degradation. If the tension is larger than the above range, wire 30 may leave its bite mark on resin film 20b.

Then as step (S50) a degradation determination step is performed. This step (S50) is performed as follows: Wire 30, with a prescribed tension F applied thereto, is accordingly displaced by an amount, which is held for a predetermined period of time, and thereafter, a tension $F_C$ applied at that time to wire 30 is read by tension gauge 9 and a tension relieved $F_1=F-F_C$ is calculated. Furthermore, it is compared with a predetermined reference, i.e., a tension relieved $F_{R0}=F_0-F_{C0}$, to determine how resin film 20b is degraded. In the present embodiment the method for detecting degradation of resin film for example uses values $F_R$ and $F_{R0}$ to calculate a rate of change in tension relieved (in %)=$|F_{R0}-F_R|/F_{R0} \times 100$ to determine how resin film 20b is degraded. Specifically, when a rate of change in tension relieved, as calculated, exceeds a prescribed value, it is determined that the rope should be repaired, replaced or similarly handled. Note that the reference value or tension relieved $F_{R0}$ may be that required to tension wire 30, as prescribed, for resin film 20b of resin coated rope 20 that is unused The present embodiment provides a method for detecting degradation of resin film, that compares tension relieved $F_R$ required to tension wire 30, as prescribed, for resin film 20b with tension relieved $F_{R0}$ required, as previously determined as a reference, to tension wire 30, as prescribed, for resin film 20b to determine how resin film 20b is degraded. Thus the present embodiment provides a method for detecting degradation of resin film, that can detect with high precision and non-destructively whether resin coated rope 20 has resin film 20b degraded, while allowing wire 30 to be tensioned, as prescribed, by a load set below that which breaks wire 30 to ensure avoiding breaking wire 30.

Fourth Embodiment

Hereinafter, the present invention in still another, fourth embodiment will be described. Initially will be described a degradation detection apparatus of the present embodiment to detect degradation of resin film. The present embodiment provides a degradation detection apparatus 2 to detect degradation of resin film, that is basically similar in configuration to the first embodiment's degradation detection apparatus 1 detecting degradation of resin film, and that is as effective as degradation detection apparatus 1 of the first embodiment. Degradation detection apparatus 2 according to the present embodiment to detect degradation of resin film, however, is different from degradation detection apparatus 1 of the first embodiment in that the former allows wire 30 to have opposite ends both displaced.

Figure 9:
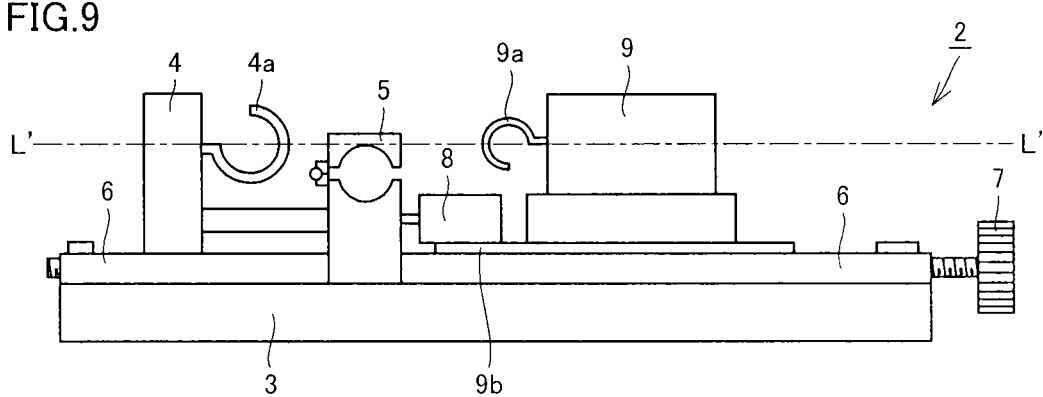
FIG. 9 is a schematic side view in configuration of a degradation detection apparatus of a fourth embodiment.
Figure 10:
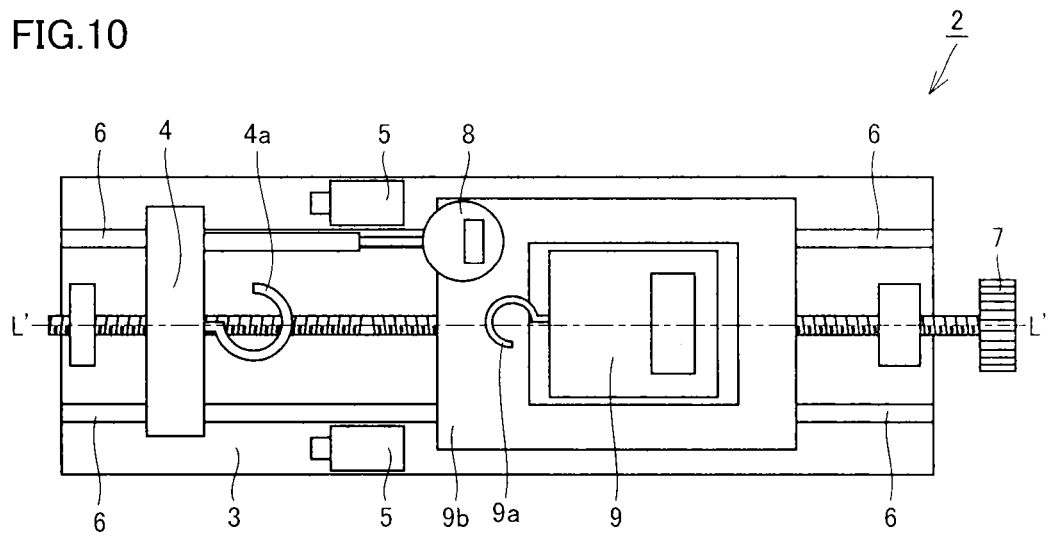
FIG. 10 is a schematic top view in configuration of the degradation detection apparatus of the fourth embodiment.

With reference to FIG. 9 and FIG. 10, degradation detection apparatus 2 mainly includes mount 3, hook support 4, hooks 4a and 9a, a plurality of rope securing units 5, linear guide 6, feed screw 7, displacement gauge 8, tension gauge 9, and a tension gauge mount 9b.

On mount 3 are disposed rope securing units 5, linear guide 6, and feed screw 7. On linear guide 6 are disposed hook support 4 to support hook 4a, and tension gauge mount 9b. On tension gauge mount 9b are disposed displacement gauge 8 and tension gauge 9 having hook 9a. Tension gauge 9 is provided with displacement gauge 8 to thereby allow how much amount tension gauge 9 has displaced to be measurable. Furthermore, tension gauge 9 has hook 9a attached thereto. Furthermore, as shown in FIG. 10, linear guide 6 is disposed on mount 3 such that linear guide 6 has its axis in a direction parallel to a virtual straight line L'-L' connecting hook 4a and hook 9a Furthermore, a plurality of (or two) rope securing units 5 are aligned on mount 3 in a direction transverse to virtual straight line L'-L', more specifically perpendicular thereto.

Similarly as has been described in the first embodiment, rope securing unit 5 fixes a relative positional relationship between a resin coated rope to be inspected and degradation detection apparatus 2. Furthermore, similarly as has been described in the first embodiment, hooks 4a and 9a hold a wire or the like wound on a circumferential portion of the resin coated rope to be secured to rope securing unit 5.

Feed screw 7 is disposed through hook support 4 and tension gauge mount 9b. Furthermore, feed screw 7 at a portion passing through hook support 4 is threaded in a direction and at that passing through tension gauge mount 9b is threaded in an opposite direction. Turning screw 7 allows hook support 4 and tension gauge mount 9b to be displaced along the axis of linear guide 6 in opposite directions (i.e., directions opposite by 180 degrees), respectively. This allows the wire held by hooks 4a and 9a to have its opposite ends both displaced. This allows the wire to be tensioned and the resin coated rope to have the circumferential coating of resin film compressed. Note that, similarly as has been described in the first embodiment, degradation detection apparatus 2 may have feed screw 7 replaced with a small servo-motor or a similar electrical mechanism allowing hook support 4 and tension gauge mount 9b to be displaceable.

Similarly as has been described in the first embodiment, tension gauge 9 detects how much tension is applied to the wire held by hooks 4a and 9a. Displacement gauge 8 detects how much amount hook support 4 and tension gauge mount 9b have relatively displaced, i.e., how much amount the wire has displaced.

Hereinafter will be described a method according to the present embodiment for detecting degradation of resin film. The present embodiment provides a method for detecting degradation of resin film, that basically includes steps similar to those of the methods according to the first and second embodiments for detecting degradation of resin film and that is as effective as the methods according to the first and second embodiments. The method according to the present embodiment, however, is different from those of the first and second embodiments in that the former includes a resin film compression step allowing a wire to have its opposite ends both displaced.

Figure 11:
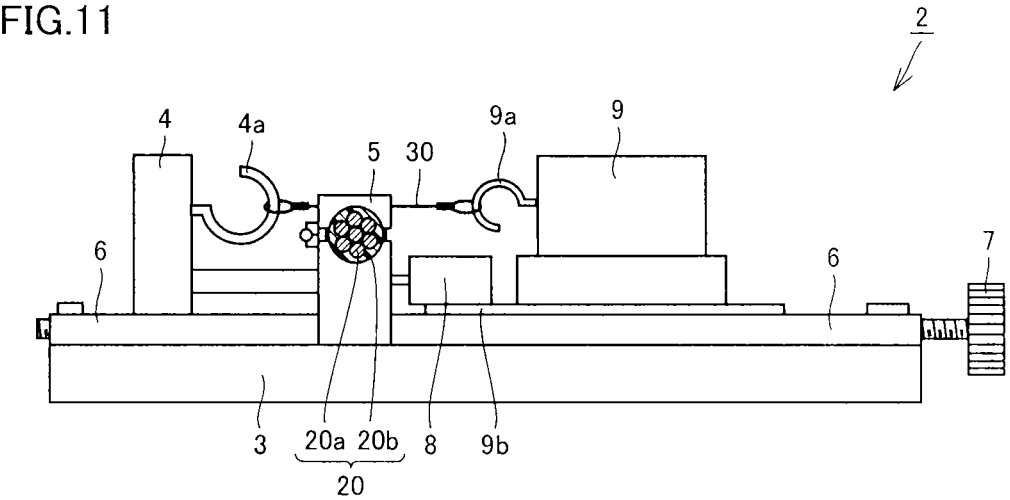
FIG. 11 is a schematic side view for illustrating a degradation detection method of the fourth embodiment.
Figure 12:
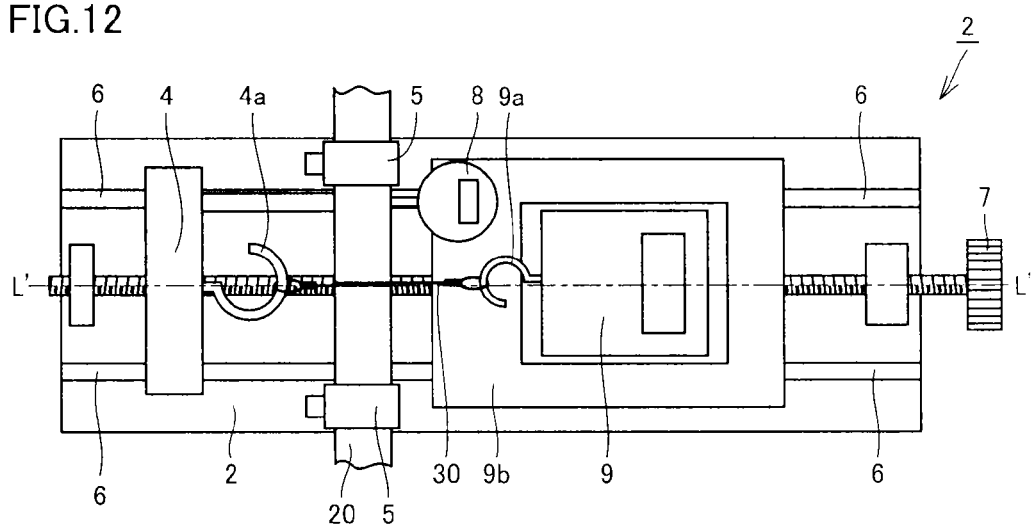
FIG. 12 is a schematic top view for illustrating the degradation detection method of the fourth embodiment.

The degradation detection method of the present embodiment is performed for example by employing degradation detection apparatus 2 of the present embodiment. With reference to FIGS. 3, 11 and 12, steps (S10) to (S30) are initially performed, similarly as has been described in the first and second embodiments.

Then as step (S40) a resin film compression step is performed. In this step (S40), with reference to FIGS. 11 and 12, feed screw 7 is turned to displace hook support 4 and tension gauge mount 9b along the axis of linear guide 6 in opposite directions (i.e., directions opposite by 180 degrees), respectively, to displace wire 30, as prescribed. More specifically, feed screw 7 is turned to allow wire 30 to have the opposite ends that are held by hooks 4a and 9a both displaced, as prescribed. This tensions wire 30, which in turn compresses resin film 20b in the radial direction of resin coated rope 20. How much amount wire 30 has displaced, i.e., how much amount resin film 20b has compressed, is detected by displacement gauge 8, and how much tension is applied to wire 30 is detected by tension gauge 9.

Then as step (S50) a degradation determination step is performed. In this step (S50), similarly as has been described in the first embodiment, tension value (F) of wire 30 required in step (S40) to compress resin film 20b by a prescribed amount is compared with tension value ($F_0$) of wire 30 required, as previously determined as a reference, to compress resin film 20b by the prescribed amount to determine how resin film 20b is degraded.

Furthermore, in this step (S50), similarly as has been described in the second embodiment, how much amount resin film 20b is required to have compressed in step (S40) to tension wire 30, as prescribed (i.e., displacement required L), may be compared with how much amount resin film 20b is required to have compressed, as previously determined as a reference, to tension wire 30, as prescribed (i.e., displacement required $L_0$), to determine how resin film 20b is degraded.

Furthermore, step (S50) may be performed as follows: Similarly as has been described in the third embodiment, step (S40) is performed to tension wire 30, as prescribed. Wire 30 is thus displaced by an amount, which may be held for a predetermined period of time, and thereafter, tension $F_C$ applied at that time to wire 30 may be read by tension gauge 9, and tension relieved $F_R = F - F_C$ may be calculated and compared with a predetermined reference, i.e., tension relieved $F_{R0} = F_0 - F_{C0}$, to determine how resin film 20b is degraded.

Thus the present embodiment provides a method for detecting degradation of resin film, that includes step (S40) to allow wire 30 to have opposite ends both displaced to thus tension wire 30 to compress resin film 20b in the radial direction of resin coated rope 20. This reduces frictional force between wire 30 and resin film 20b more than when wire 30 has only one end displaced. Thus the present embodiment provides a method for detecting degradation of resin film, that can limit the noise otherwise attributed to that frictional force and detect with higher precision whether resin film 20b is degraded.

EXAMPLES

Example 1

Degradation detection apparatus 1 of the first to third embodiments was employed. A wire with an outer diameter of 0.25 mm and a length of 300 mm was used. Inspected were an unused resin coated rope, a resin coated rope equivalent to that used for 5 years, and a resin coated rope equivalent to that used for 10 years. Initially, a resin coated rope was secured to the rope securing unit, and the tension gauge's value was corrected to zero. Then, the wire was wound on the circumferential portion of the resin coated rope and had opposite ends engaged with and thus held by the hooks, respectively. Then the feed screw was turned to allow the wire to have one end displaced to cause the wire to experience a tension of 0.5 N to thus wind the wire in a condition as shown in FIG. 6. Then, the displacement and tension gauges had their respective values corrected to zero. Then, the feed screw was turned to displace the wire to cause the displacement gauge to attain a value of 0.5 mm, when tension value (F) was measured with the tension gauge. The unused resin coated rope similarly had its tension value ($F_0$) measured, and a rate of change in tension (in %) = $|F_0 - F|/F_0 \times 100$ was calculated. Table 1 indicates the tension value (F) and rate of change in tension (in %) of the unused resin coated rope, those of the resin coated rope equivalent to that used for 5 years, and those of the resin coated rope equivalent to that used for 10 years, as measured.

TABLE 1

| | unused product | product equivalent to that used for 5 years | product equivalent to that used for 10 years |
|---|---|---|---|
| tension (N) | 2.23 | 4.22 | 5.62 |
| rate of change in tension (%) | 0 | 89 | 152 |

Example 2

A degradation detection apparatus, a wire, and a resin coated rope that were similar to those of example 1 were used. Initially, the resin coated rope was secured to the rope securing unit, and the tension gauge's value was corrected to zero. Then, the wire was wound on the circumferential portion of the resin coated rope and had opposite ends engaged with and thus held by the hooks, respectively. Then the feed screw was turned to displace the wire to cause the wire to experience a tension of 0.5 N to thus wind the wire in the condition as shown in FIG. 6. Then, the displacement and tension gauges had their respective values corrected to zero. Then, the feed screw was turned to cause the tension gauge to attain a value of 8 N and thus allow the wire to have one end displaced, when how much amount the resin film had compressed (i.e., displacement required L) was measured. The unused resin coated rope similarly had how much amount its resin film had compressed (i.e., displacement required $L_0$) measured, and a rate of change in displacement required (in %)=$|L_0-L|/L_0 \times 100$ was calculated. Table 2 indicates the displacement required (L) and rate of change in displacement required (in %) of the resin film of the unused resin coated rope, those of the resin film of the resin coated rope equivalent to that used for 5 years, and those of the resin film of the resin coated rope equivalent to that used for 10 years, as measured.

TABLE 2

|  | unused product | product equivalent to that used for 5 years | product equivalent to that used for 10 years |
|---|---|---|---|
| displacement required (mm) | 1.35 | 0.89 | 0.68 |
| rate of change in displacement required (%) | 0 | 34 | 50 |

Example 3

A degradation detection apparatus, a wire, and a resin coated rope that were similar to those of example 1 were used. Initially, the resin coated rope was secured to the rope securing unit, and the tension gauge's value was corrected to zero. Then, the wire was wound on the circumferential portion of the resin coated rope and had opposite ends engaged with and thus held by the hooks, respectively. Then the feed screw was turned to displace the wire to cause the wire to experience a tension of 0.5 N to thus wind the wire in the condition as shown in FIG. 6. Then, the displacement and tension gauges had their respective values corrected to zero. Then, the feed screw was turned to cause the tension gauge to attain a value of 8 N and thus allow the wire to have one end displaced. The wire was thus displaced by an amount, which was in turn held for 60 seconds, and thereafter, tension $F_C$ applied at that time to the wire was read by the tension gauge and tension relieved $F_R=8-F_C$ was calculated. The unused resin coated rope similarly had its tension relieved $F_{R0}$ measured, and a rate of change in tension relieved (in %)=$|F_{R0}-F_R|/F_{R0} \times 100$ was calculated. Table 3 indicates the tension relieved $F_R$ and rate of change in tension relieved (in %) of the resin film of the unused resin coated rope, those of the resin film of the resin coated rope equivalent to that used for 5 years, and those of the resin film of the resin coated rope equivalent to that used for 10 years, as measured.

TABLE 3

|  | unused product | product equivalent to that used for 5 years | product equivalent to that used for 10 years |
|---|---|---|---|
| tension relieved (N) | 1.86 | 1.49 | 1.39 |
| rate of change in tension relieved (%) | 0 | 20 | 25 |

Example 4

Degradation detection apparatus 2 of the fourth embodiment was used. A wire and a resin coated rope that were similar to those of example 1 were used. Initially, the resin coated rope was secured to the rope securing unit, and the tension gauge's value was corrected to zero. Then, the wire was wound on the circumferential portion of the resin coated rope and had opposite ends engaged with and thus held by the hooks, respectively. Then the feed screw was turned to allow the wire to have the opposite ends displaced to cause the wire to experience a tension of 0.5 N to thus wind the wire in the condition as shown in FIG. 6. Then, the displacement and tension gauges had their respective values corrected to zero. Then, the feed screw was turned to displace the wire to cause the displacement gauge to attain a value of 0.5 mm, when tension value (F) was measured with the tension gauge. The unused resin coated rope similarly had its tension value ($F_0$) measured, and a rate of change in tension (in %)=$|F_0-F|/F_0 \times 100$ was calculated. Table 4 indicates the tension value (F) and rate of change in tension (in %) of the unused resin coated rope, those of the resin coated rope equivalent to that used for 5 years, and those of the resin coated rope equivalent to that used for 10 years, as measured.

TABLE 4

|  | unused product | product equivalent to that used for 5 years | product equivalent to that used for 10 years |
|---|---|---|---|
| tension (N) | 2.04 | 4.30 | 5.68 |
| rate of change in tension (%) | 0 | 111 | 178 |

Example 5

A degradation detection apparatus, a wire, and a resin coated rope that were similar to those of example 4 were used. Initially, the resin coated rope was secured to the rope securing unit, and the tension gauge's value was corrected to zero. Then, the wire was wound on the circumferential portion of the resin coated rope and had opposite ends engaged with and thus held by the hooks, respectively. Then the feed screw was turned to displace the wire to cause the wire to experience a tension 0.5 N to thus wind the wire in the condition as shown in FIG. 6. Then, the displacement and tension gauges had their respective values corrected to zero. Then, the feed screw was turned to cause the tension gauge to attain a value of 8 N and thus allow the wire to have the opposite ends displaced, when how much amount the resin film had compressed (i.e., displacement required L) was measured. The unused resin coated rope similarly had how much amount its resin film had compressed (i.e., displacement required $L_0$) measured, and a rate of change in displacement required (in %)=$|L_0-L|/L_0 \times 100$ was calculated. Table 5 indicates the displacement required (L) and rate of change in displacement required (in %) of the resin film of the unused resin coated rope, those of the resin film of the resin coated rope equivalent to that used for 5 years, and those of the resin film of the resin coated rope equivalent to that used for 10 years, as measured.

TABLE 5

|  | unused product | product equivalent to that used for 5 years | product equivalent to that used for 10 years |
|---|---|---|---|
| displacement required (mm) | 1.35 | 0.94 | 0.73 |
| rate of change in displacement required (%) | 0 | 30 | 46 |

Example 6

A degradation detection apparatus, a wire, and a resin coated rope that were similar to those of example 4 were used. Initially, the resin coated rope was secured to the rope securing unit, and the tension gauge's value was corrected to zero. Then, the wire was wound on the circumferential portion of the resin coated rope and had opposite ends engaged with and thus held by the hooks, respectively. Then the feed screw was turned to displace the wire to cause the wire to experience a tension of 0.5 N to thus wind the wire in the condition as shown in FIG. 6. Then, the displacement and tension gauges had their respective values corrected to zero. Then, the feed screw was turned to cause the tension gauge to attain a value of 8 N and thus allow the wire to have the opposite ends displaced. The wire was thus displaced by an amount, which was in turn held for 60 seconds, and thereafter, tension $F_C$ applied at that time to the wire was read by the tension gauge and tension relieved $F_R = 8 - F_C$ was calculated. The unused resin coated rope similarly had its tension relieved $F_{R0}$ measured, and a rate of change in tension relieved (in %)=$|F_{R0}-F_R|/F_{R0} \times 100$ was calculated. Table 6 indicates the tension relieved $F_R$ and rate of change in tension relieved (in %) of the resin film of the unused resin coated rope, those of the resin film of the resin coated rope equivalent to that used for 5 years, and those of the resin film of the resin coated rope equivalent to that used for 10 years, as measured.

TABLE 6

|  | unused product | product equivalent to that used for 5 years | product equivalent to that used for 10 years |
|---|---|---|---|
| tension relieved (N) | 1.82 | 1.40 | 1.28 |
| rate of change in tension relieved (%) | 0 | 23 | 30 |

Comparative Example

Examples 1-6 were compared with a comparative example: an unused resin coated rope, a resin coated rope equivalent to that used for 5 years, and a resin coated rope equivalent to that used for 10 years having their respective resin films measured in indentation hardness via a type-A hardness meter. Furthermore, the resin coated ropes also had their respective rates of change in indentation hardness calculated (in %) with reference to the indentation hardness of the unused product. Table 7 indicates the indentation hardness and rate of change in indentation hardness (in %) of the resin film of the unused resin coated rope, those of the resin film of the resin coated rope equivalent to that used for 5 years, and those of the resin film of the resin coated rope equivalent to that used for 10 years, as measured.

TABLE 7

|  | unused product | product equivalent to that used for 5 years | product equivalent to that used for 10 years |
|---|---|---|---|
| A hardness | 93 | 94 | 93 |
| rate of change in A hardness (%) | 0 | 1 | 0 |

As is apparent from table 1 to table 7, the comparative example indicated that the unused resin coated rope, the resin coated rope equivalent to that used for 5 years, and the resin coated rope equivalent to that used for 10 years presented their respective rates of change in indentation hardness, as calculated, without a large difference therebetween, whereas examples 1-6 indicated that the unused resin coated rope, the resin coated rope equivalent to that used for 5 years, and the resin coated rope equivalent to that used for 10 years presented their respective rates of change in tension and in how much amount their respective resin films had compressed, as calculated, with a large difference therebetween. Thus it has been confirmed that the present method for detecting degradation of resin film can detect with high precision whether a resin coated rope has a resin film degraded.

It should be understood that the embodiments and examples disclosed herein have been described for the purpose of illustration only and in a non-restrictive manner in any respect. The scope of the present invention is defined by the terms of the claims, rather than the description above, and is intended to include any modifications within the meaning and scope equivalent to the terms of the claims.

INDUSTRIAL APPLICABILITY

The present method and apparatus for detecting degradation of resin film is particularly advantageously applicable to a method and apparatus required to detect with high precision and non-destructively whether a resin coated rope has a resin film degraded.

REFERENCE SIGNS LIST

1, 2: degradation detection apparatus; 3: mount; 4: hook support; 4a, 9a: hook; 5: rope securing unit; 6: linear guide; 7: feed screw; 8: displacement gauge; 9: tension gauge; 9b: tension gauge mount; 20: resin coated rope; 20a: steel wire; 20b: resin film; 30: wire.

The invention claimed is:

1. A method for detecting degradation of resin film to detect whether a resin coated rope for an elevator, that has a circumferential portion coated with resin film and internally has a twisted steel wire bundle, has said resin film degraded, comprising:

winding a linear object on said circumferential portion of said resin coated rope;

applying tension to said linear object to compress said resin film along an entire circumference of said resin coated rope in a radial direction of said resin coated rope; and comparing a first relationship with a second relationship to determine how said resin film is degraded, said first relationship indicating a relationship between said tension of said linear object and how much amount said resin film has compressed, as obtained in the applying, said second relationship indicating a relationship between said tension of said linear object and said how much amount said resin film has compressed, as predetermined as a reference, wherein said linear object is a wire having an outer diameter of 0.1-1.0 mm, wherein said resin film is thermoplastic polyurethane elastomer, and wherein comparing a first relationship with a second relationship to determine how said resin film is degraded includes comparing a rate of change obtained by dividing an absolute value of a difference between a value of said first relationship and a value of said second relationship by said value of said second relationship with a predetermined rate of change to determine how said resin film is degraded.

2. The method for detecting degradation of resin film according to claim 1, wherein said second relationship is a relationship between said tension of said linear object and said how much amount said resin film has compressed, as obtained when said resin coated rope is unused.

3. The method for detecting degradation of resin film according to claim 1, wherein:
said first relationship is obtained in the step of applying by applying said tension, as prescribed, to said linear object to provide and hold said how much amount said resin film has compressed for a predetermined period of time, and thereafter obtaining by how much amount said tension applied to said linear object has varied from that applied thereto before said predetermined period of time is counted to serve as said first relationship; and
said second relationship is a reference predetermined by applying said tension, as prescribed, to said linear object to provide and hold said how much amount said resin film has compressed for said predetermined period of time, and thereafter obtaining by how much amount said tension applied to said linear object has varied from that applied thereto before said predetermined period of time is counted to serve as said second relationship.

4. The method for detecting degradation of resin film according to claim 1, wherein:
said first relationship is a value of said tension of said linear object, as applied in the applying, required to compress said resin film by a prescribed amount; and
said second relationship is a value of said tension of said linear object, as predetermined as a reference, required to compress said resin film by said prescribed amount.

5. The method for detecting degradation of resin film according to claim 1, wherein:
said first relationship is a value of said how much amount said resin film has compressed, as applied in the applying, required to cause said linear object to experience said tension, as prescribed; and
said second relationship is a value of said how much amount said resin film has compressed, as predetermined as a reference, required to cause said linear object to experience said tension, as prescribed.

6. An apparatus for detecting degradation of resin film to detect whether a resin coated rope for an elevator, that has a circumferential portion coated with resin film and internally has a twisted steel wire bundle, has said resin film degraded, the apparatus comprising:
a securing unit that fixes a relative positional relationship between said resin coated rope and the apparatus;
a holding unit capable of holding a linear object wound on said circumferential portion of said resin coated rope;
a tensioning unit applying tension to said linear object;
a tension detection unit that detects said tension applied to said linear object; and
a displacement detection unit that detects how much amount said linear object has displaced,
wherein said linear object is a wire having an outer diameter of 0.1-1.0 mm,
wherein said resin film is thermoplastic polyurethane elastomer, and
wherein said holding unit is provided as a pair of such holding units to sandwich said securing unit, wherein said pair of holding units has at least one holding unit displaceable relative to the other holding unit different from said one holding unit.

7. An apparatus for detecting degradation of resin film to detect whether a resin coated rope for an elevator, that has a circumferential portion coated with resin film and internally has a twisted steel wire bundle, has said resin film degraded, the apparatus comprising:
a securing unit that fixes a relative positional relationship between said resin coated rope and the apparatus;
a holding unit capable of holding a linear object wound on said circumferential portion of said resin coated rope;
a tensioning unit applying tension to said linear object;
a tension detection unit that detects said tension applied to said linear object; and
a displacement detection unit that detects how much amount said linear object has displaced,
wherein said linear object is a wire having an outer diameter of 0.1-1.0 mm,
wherein said resin film is thermoplastic polyurethane elastomer, and
wherein said holding unit is provided as a pair of such holding units to sandwich said securing unit, wherein said securing unit is a plurality of such securing units aligned in a direction transverse to a virtual straight line connecting one holding unit of said pair of holding units and the other holding unit different from said one holding unit.

8. An apparatus for detecting degradation of resin film to detect whether a resin coated rope for an elevator, that has a circumferential portion coated with resin film and internally has a twisted steel wire bundle, has said resin film degraded, the apparatus comprising:
a securing unit that fixes a relative positional relationship between said resin coated rope and the apparatus;
a holding unit capable of holding a linear object wound on said circumferential portion of said resin coated rope;
a tensioning unit applying tension to said linear object;
a tension detection unit that detects said tension applied to said linear object; and
a displacement detection unit that detects how much amount said linear object has displaced,
wherein said linear object is a wire having an outer diameter of 0.1-1.0 mm,
wherein said resin film is thermoplastic polyurethane elastomer, and
wherein said apparatus compares a rate of change obtained by dividing an absolute value of a difference between a value of a first relationship representing a relationship between said second tension of said linear object applied to compress said resin film and how much said resin film is compressed, and a value of a second relationship predetermined as a reference and representing a relationship between said second tension of said linear object and how much said resin film is compressed, by said value of said second relationship, with a predetermined rate of change to determine how said resin film is degraded.

* * * * *